(12) United States Patent
Saladino

(10) Patent No.: US 6,749,638 B1
(45) Date of Patent: Jun. 15, 2004

(54) MODULAR KNEE PROSTHESIS

(75) Inventor: Joseph Saladino, Pflugerville, TX (US)

(73) Assignee: Zimmer Technology, Inc., Chicago, IL (US)

( * ) Notice: Subject to any disclaimer, the term of this patent is extended or adjusted under 35 U.S.C. 154(b) by 6 days.

(21) Appl. No.: 10/302,066

(22) Filed: Nov. 22, 2002

(51) Int. Cl.[7] ................................................ A61F 2/38
(52) U.S. Cl. ................................................ 623/20.14
(58) Field of Search ................... 623/20.14, 20.15–20.3

(56) References Cited

U.S. PATENT DOCUMENTS

| | | | | |
|---|---|---|---|---|
| 5,258,032 A | * | 11/1993 | Bertin | 623/20.35 |
| 5,776,201 A | * | 7/1998 | Colleran et al. | 623/20.15 |
| 6,402,786 B1 | * | 6/2002 | Insall et al. | 623/20.35 |
| 2003/0093156 A1 | * | 5/2003 | Metzger et al. | 623/20.15 |
| 2003/0158606 A1 | * | 8/2003 | Coon et al. | 623/20.15 |
| 2003/0225457 A1 | * | 12/2003 | Justin et al. | 623/20.14 |

\* cited by examiner

*Primary Examiner*—Suzette J. Jackson
(74) *Attorney, Agent, or Firm*—Jonathan D. Feuchtwang; Zimmer Technology, Inc.

(57) ABSTRACT

A modular knee prosthetic system used to replace the natural knee and including two distal posterior femoral components and one patellar-femoral joint component. The components have a smooth outer condylar surface and an inner bone-engaging surface and are connectable to form either an unicompartmental or bicompartmental femoral knee prosthesis.

12 Claims, 8 Drawing Sheets

MODULAR KNEE PROSTHESIS

FIELD OF THE INVENTION

The present invention relates to a modular knee prosthetic system used to replace the natural knee and, more particularly, to a unicompartmental and bicompartmental modular knee system having various distal posterior femoral components that are interchangeable with each other and with various patellar-femoral joint components.

BACKGROUND OF THE INVENTION

In knee arthroplasty, portions of the natural knee joint are replaced with prosthetic knee components. Typically, these components include a tibial component, a femoral component, and a patellar component. The femoral component generally includes a pair of spaced condyles that articulate with the tibial component. The components are made of materials that exhibit a low coefficient of friction when they articulate against one another.

When the articulating ends of both the femur and tibia are replaced, the procedure is referred to as total knee replacement or TKR. Much effort has been devoted to performing a TKR that restores normal, pain-free, functions of the knee in a short period of postoperative time.

Several factors lead to long-term success of TKR. One important factor is soft-tissue balancing. The normal, non-diseased knee is considered properly balanced when the deflection between the medial and lateral condyles and the tibial plateau is equal throughout the entire range of motion. If this balance is not achieved, abnormal knee kinematics occurs, and the TKR components and surrounding soft tissue can experience excessive forces even during normal range of motion. These excessive forces can further cause an abnormal gait, pain, and early failure of total knee replacements.

Soft-tissue balancing can be achieved in TKR if the components are correctly sized and properly placed. In order to achieve proper placement during a TKR surgery, equal tibial-femoral flexion gaps and extension gaps must be achieved. The flexion gap is defined as the space between the posterior coronal cut on the distal femur and transverse cut on the proximal tibia, while the knee is in 90° of flexion. The extension gap is defined as the space between the transverse cut on distal femur and the transverse proximal tibial cut while the knee is in complete extension. Soft tissue balance occurs when stability is achieved in both flexion and extension.

During a TKR surgery, a series of surgical compromises is often used to achieve a balance of flexion and extension gaps. Elevation of the joint line is one such compromise. An elevation of the joint line occurs when there is a change in distance from the original articular surface to the newly reconstructed surface. This change in distance is typically measured as a vertical distance from a fixed point on the tibia.

For several reasons, the joint line can become elevated. Excessive medial or lateral releases and insertion of thicker plastic inserts can cause the line to elevate. Further, the joint line can become elevated when the femoral component is undersized. Such an undersize can create a larger flexion gap than extension gap. To balance these gaps, more bone may need to be removed from the distal femur; and this additional bone loss raises the joint line.

Unfortunately, a change in the joint line can negatively affect a wide array of components and operations of the knee, such as the functions of the PCL, collateral ligaments, and patello-femoral joint mechanics. These problems can be avoided or minimized if elevation of the joint line is reduced or, better yet, eliminated.

Another surgical compromise often occurs when soft tissue gaps are balance when implanting a distal femoral knee prosthesis. A healthy balance of these gaps maintains the natural kinematics of the patient. The compromise occurs when the operating surgeon must choose one of six or seven differently sized distal femur prostheses; and the size of these prostheses may not exactly match the size of an ideal prosthesis for the patient. For example, current anterior referencing methodology to achieve balanced flexion and extension gaps in most patients requires the surgeon to slightly alter the joint line. If an anterior referencing sizing guide falls between two sizes, the surgeon could be forced to choose a smaller size prosthesis so the flexion gap is not overstuffed. A smaller prosthesis, in such an instance however, can consequently enlarge the flexion gap as much as 3.5 mm to 4 mm.

Another important factor that contributes to the long-term success of total knee replacements is loading and kinematics of the patellar-femoral joint. Complications associated with patella failures account for up to 50% of TKR revision procedures. Many of these complications occur because of improper or unnatural loading or kinematics of the patellar-femoral joint. For example, overstuffing the patellar-femoral joint is one major cause of improper soft tissue loading and kinematics. In this regard, many surgeons use posterior referencing instrumentation when sizing and preparing the femur for implant resurfacing. On the one hand, posterior referencing allows the surgeon to balance the tibial-femoral flexion and extension gaps without necessarily changing the joint line. On the other hand though, the use of posterior referencing increases the risk of notching the anterior cortex and overstuffing the patellar-femoral joint.

In short, current knee systems often require an unwanted surgical compromise. Such compromises can alter the natural joint line of the patient or overstuff the patellar-femoral joint. Unfortunately, these compromises also negatively affect the natural kinematics of the patient and can, for example, increase strain on the PCL and other tendons and ligaments, increase implant wear, and decrease implant function. Patients may be more likely to experience pain, reduced function, and more frequent revision surgeries.

Current knee systems have other disadvantages as well. Distal femoral prostheses are simply too large to fit through small incisions that are used during a minimally invasive surgery or MIS. MIS has many advantages over traditional surgical techniques since it provides shorter incisions, faster recovery times, and generally less pain for the patient. The surgical technique, though, has limitations. As noted, current tricompartmental distal femoral prostheses cannot fit through the small incision, usually three inches in length. To date, MIS has been generally limited to unicondylar or unicompartmental knee replacement prostheses that are much smaller in size and able to fit through the incision.

It would be advantageous to have a modular knee prosthetic system that has advantages over prior knee prosthetic systems and techniques. Such a system would have greater modular versatility to accommodate different patient anatomies and joint conditions while maintaining a relatively low component count.

SUMMARY OF THE INVENTION

The present invention is directed toward a modular knee system having various distal posterior femoral components that are interchangeable with each other and with various patellar-femoral joint components. Preferably, the modular knee system has a variety of components that are interchangeable and connectable to resurface the distal femur using either a unicompartmental femoral knee prosthesis or a bicompartmental femoral knee prosthesis. These components include a medial distal posterior femoral component, a lateral distal posterior femoral component, a patellar-femoral joint component, and an interconnection mechanism to modularly connect the components together.

The knee system of the present invention allows for modularity between the distal posterior femoral components and the patellar-femoral joint components. The interchangeability of these components enables mixing and matching of multiple sizes and thicknesses of all components. This interchangeability allows the surgeon to resurface the distal femur without overstuffing the patellar compartment or changing the natural tibial-femoral joint line.

One advantage of the present invention is that the modularity of components gives the surgeon more diversification when choosing sizes for the medial and lateral condyles. The deflection between these condyles and the tibial plateau, thus, can be more easily equalized throughout the range of motion. As such, the soft-tissue can be more easily balanced.

Another important advantage of the present invention is that the various knee components are interchangeable and can be more correctly sized for an accurate fit. As such, more equal tibial-femoral flexion gaps and extension gaps can be achieved. In particular, excessive medial or lateral releases and insertion of thicker plastic inserts can be more easily avoided. Elevation of the joint line in these situations can be minimized or, better yet, avoided.

Further, modularity of the knee components enables a more natural balance between soft tissue gaps when implanting a distal femoral knee prosthesis. If, for example, different sizing occurs between the medial and lateral sides of the distal posterior components, differently sized distal posterior femoral components can be connected together to accommodate this variance of sizing. Thus, differently sized condyles may be implanted on the medial and lateral sides to more closely replicate the natural anatomy of the patient. Further, additional bone may be saved and not unnecessarily removed from the distal femur or from the tibia.

Since the present invention can more readily accommodate various sizes during knee replacement surgery, the natural location of the joint line can be maintained. Certain problems associated with altering the joint line can be avoided or minimized.

The present modular knee system can also help achieve natural loading and kinematics of the patellar-femoral joint. For example, the various sizes and interchangeability of knee components can enable more correctly sized patellar-femoral joints. In some situations, overstuffing can be avoided.

As another important advantage, all of the individual components of the modular knee system of the present invention is small enough to be used during minimally invasive surgery or MIS. Each modular component can fit through a three inch incision. Even more importantly, the modular components can be assembled after being inserted through the incision. Thus, the modular knee system can be used with either unicompartmental, bicompartmental, or tricompartmental procedures (i.e., either unicondylar, bicondylar, or tricompartmental knee replacements).

As yet even another advantage, the modularity of the present knee system reduces the overall number of individual components required in a knee product line. This reduction has significant cost savings.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein.

DETAILED DESCRIPTION

Figure 1:
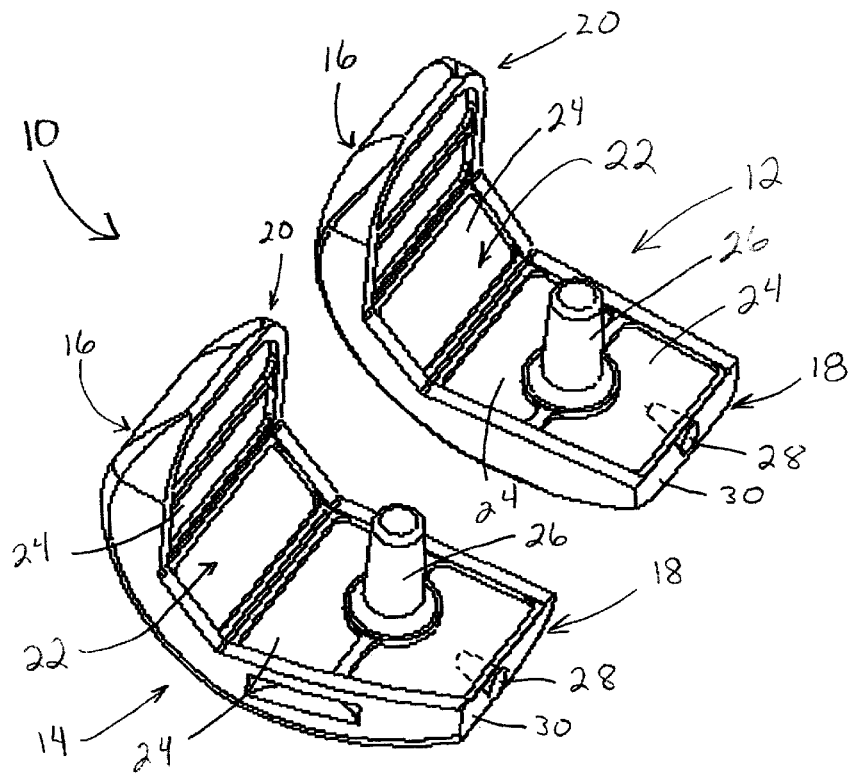
FIG. 1 illustrates a perspective view of two medial distal posterior femoral components of the present invention.
Figure 2:
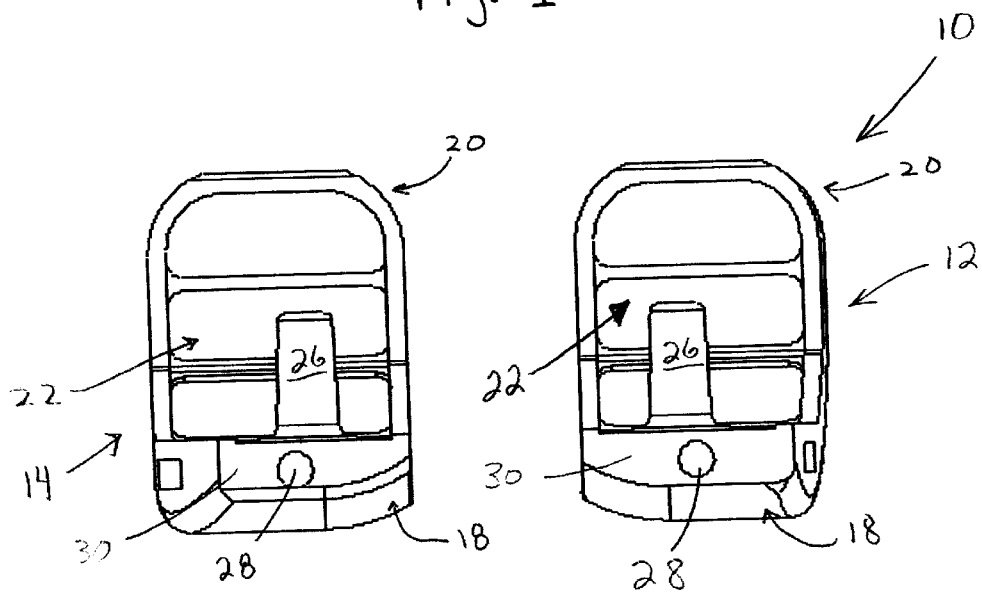
FIG. 2 illustrates a side view of the femoral components of FIG. 1.

FIGS. 1 and 2 illustrate two separate distal posterior femoral components generally at 10. One component is a medial distal posterior femoral component (DPFC) 12, and a second component is a lateral DPFC 14. Both femoral components 12 and 14 have a smooth outer condylar surface 16 adapted to articulate with a tibial insert. Surface 16 is shaped as a partial femoral condyle that extends from a proximal portion 18 to a distal portion 20. A bone engaging surface 22 is oppositely disposed from the condylar surface 16. This surface 22 includes several flat, planar sections 24 that extend from the proximal portion 18 to the distal portion 20. A stem 26 projects upwardly from the bone engaging surface 22. This stem 26 has a tapering cylindrical shape and is adapted to be inserted in the intramedullary canal of a femur.

The medial and lateral DPFC also includes a connector 28 located on an end surface 30 of the proximal portion 18. The connectors 28 are shaped as cylindrical, tapering recesses. These recesses extend into the body of the femoral components.

Figure 3:
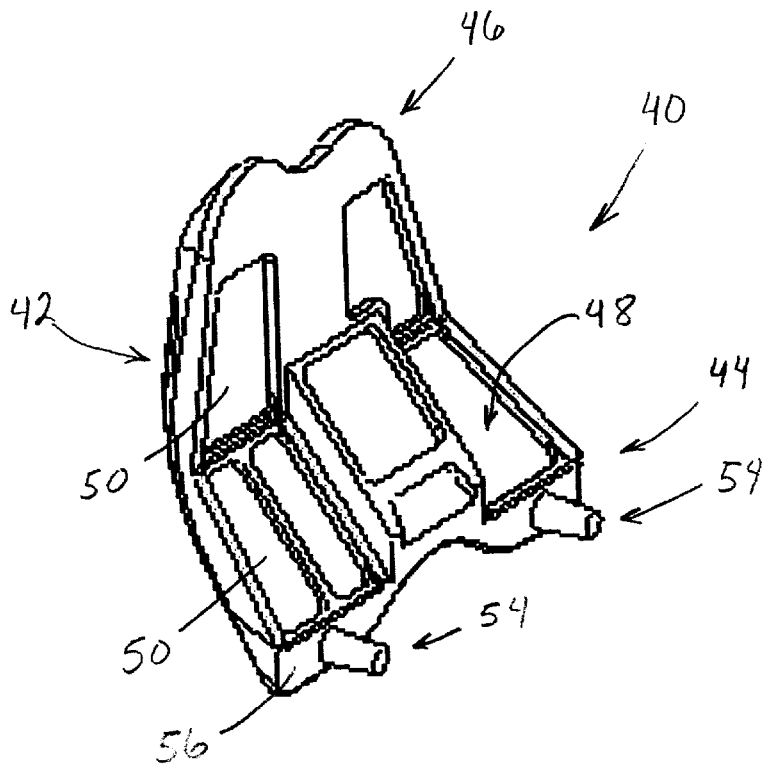
FIG. 3 illustrates a perspective view a patellar-femoral joint component of the present invention.
Figure 4:
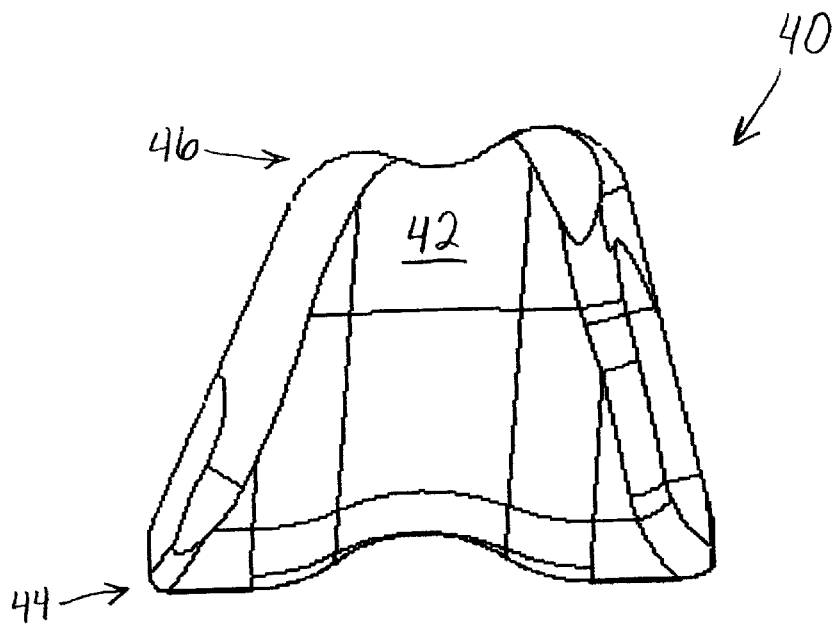
FIG. 4 illustrates the condylar surface of the patellar-femoral joint component of FIG. 3.

FIGS. 3 and 4 illustrate a patellar-femoral joint component (PFJC) 40. The PFJC 40 has a smooth outer condylar surface 42 adapted to articulate with a tibial insert. Surface 42 is shaped as a partial femoral condyle that extends from a proximal portion 44 to a distal portion 46. A bone engaging surface 48 is oppositely disposed from the condylar surface 42. This surface 48 includes several flat, planar sections 50 that extend from the proximal portion 44 to the distal portion 46.

The PFJC 40 also includes a connection mechanism 54 located on an end surface 56 of the proximal portion 44. The connection mechanism 54 is shaped as two separate, spaced projections having a cylindrical, tapering body. The projection extends outwardly from the body of the PFJC.

Figure 5:
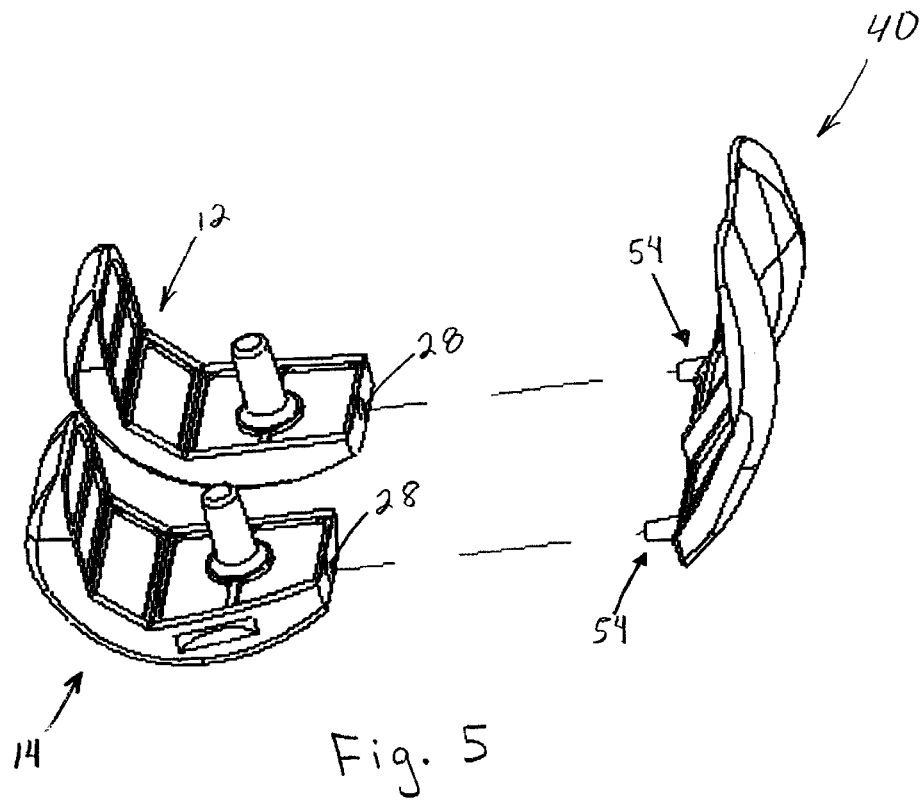
FIG. 5 illustrates an exploded view of the two medial distal posterior femoral components of FIG. 1 connecting to the patellar-femoral joint component of FIG. 3.
Figure 6:
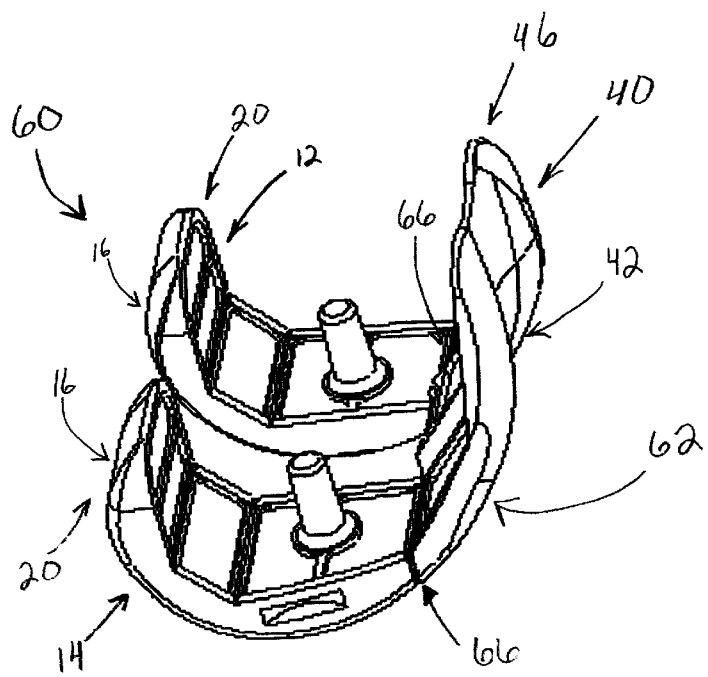
FIG. 6 illustrates a perspective view of a bicompartmental femoral knee with the two medial distal posterior femoral components of FIG. 1 connected to the patellar-femoral joint component of FIG. 3.

Turning also to FIGS. 5 and 6, connection mechanism 54 of the PFJC 40 is adapted to engage and connect with the connectors 28 on both the medial DPFC 12 and lateral DPFC 14. Specifically, the projections of the connection mechanism 54 slideably press-fit to lock into the recesses of the connectors 28. This connection may utilize a Morse taper fit.

One skilled in the art will appreciate that many different means exist for connecting the distal posterior femoral components 10 to the PFJC 40. In this regard, the connectors 28 could be configured as tapering male projections while the connection mechanism is configured as a tapering recess adapted to receive the projections. Other connections exist as well. For example, the connection mechanism could be configured to snapingly engage the connectors or configured as a bayonet type connection. Further, the connection between the connection mechanism 54 and the connectors 28 could be permanent or removeably connected.

It is important to note that when the medial DPFC 12 and the lateral DPFC 14 connect to the PFJC 40, these components form a complete, full femoral knee prosthesis 60 (see FIG. 6). This prosthesis 60 functions as a traditional one-piece bicompartmental femoral prosthesis. As such, the prosthesis 60 may be used as a bicompartmental femoral prosthesis for total knee replacements. The important advantage of the present invention, though, is that the prosthesis 60 is composed of several modular pieces. Specifically, the prosthesis is composed of three separate, interconnectable pieces, namely a medial DPFC 12, a lateral DPFC 14, and a PFJC 40.

As noted, the distal posterior femoral components have a partial condylar surface 16, and the PFJC 40 has a partial condylar surface 42. When these components are connected together to form the femoral knee prosthesis 60, then the surfaces 16 and 42 join and form a full condylar surface 62. This surface 62 extends from the distal portion 20 of the distal posterior femoral components to the distal portion 46 of the PFJC. Preferably, this surface 62 is continuous and seamless at the junction or union 66 from surface 16 to surface 42. No bumps, ridges, seams, indentations, channels, or the like should exist at the junction 66 where the surfaces meet.

Figure 7:
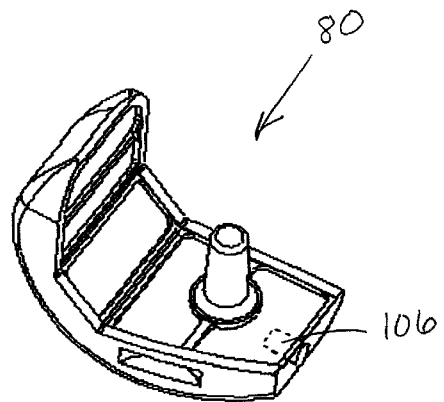
FIG. 7 illustrates a single medial distal posterior femoral component.
Figure 8:
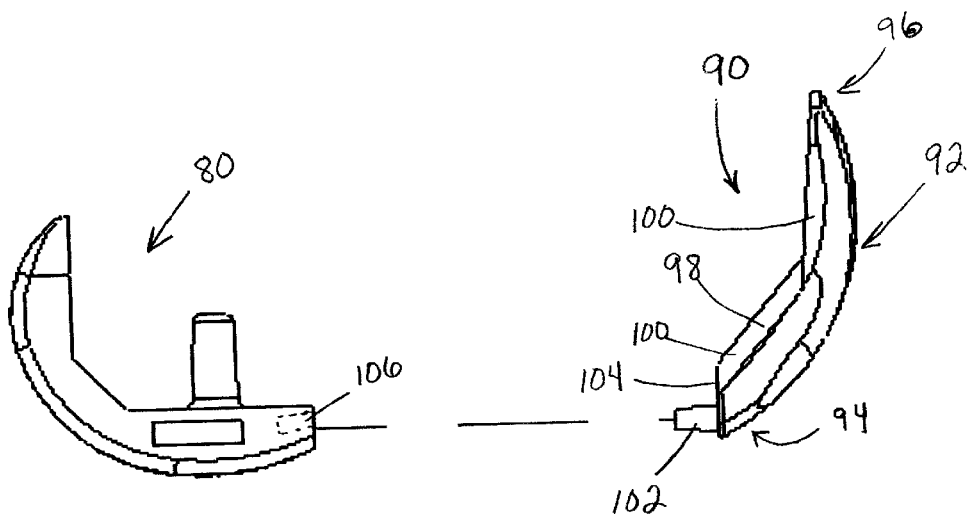
FIG. 8 illustrates an exploded view of a unicompartmental femoral knee with the single medial distal posterior femoral component of FIG. 7 and a single patellar-femoral joint component.
Figure 9:
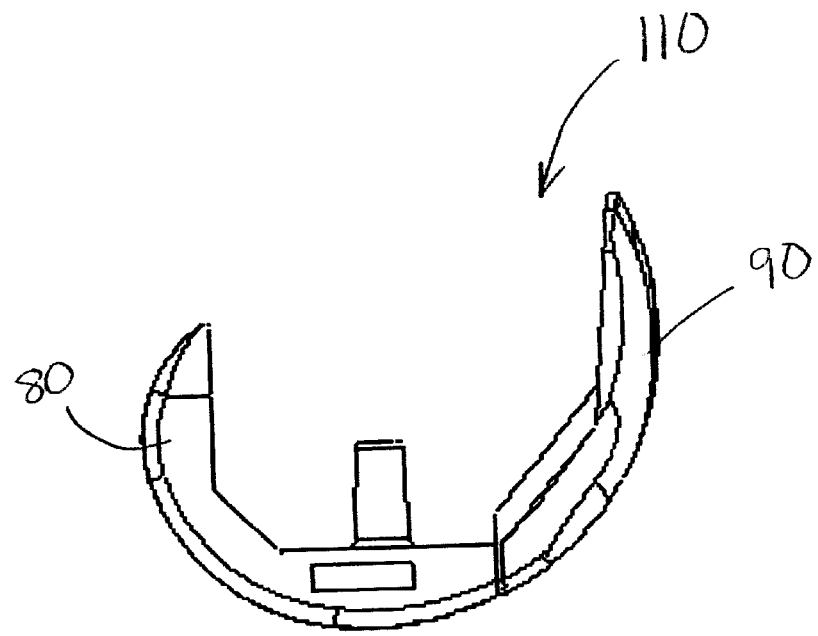
FIG. 9 illustrates a unicompartmental femoral knee with the medial distal posterior femoral component and the patellar-femoral joint component of FIG. 8 connected together.

FIGS. 7–9 illustrate one of the modular properties of the present invention. FIG. 7 shows a single distal posterior femoral component 80. DPFC 80 is similarly configured to the distal posterior femoral components shown in FIGS. 1 and 2. This component 80 may be shaped for use as a medial DPFC, lateral DPFC, or generic and useable for both medial and lateral indications.

FIG. 8 shows a patellar-femoral joint component 90 that is similarly configured to the PFJC 40 shown in FIGS. 3 and 4. One important exception is the PFJC 90 is not shaped for bicompartmental use but for unicompartmental use. More specifically, the PFJC 90 has a single smooth outer condylar surface 92 adapted to articulate with a tibial insert. Surface 92 is shaped as a partial single femoral condyle that extends from a proximal portion 94 to a distal portion 96. A bone engaging surface 98 is oppositely disposed from the condylar surface 92. This surface 98 includes several flat, planar sections 100 that extend from the proximal portion 94 to the distal portion 96. The PFJC 90 also includes a connection mechanism 102 located on an end surface 104 of the proximal portion 94. The connection mechanism 102 is shaped as a single projection having a cylindrical, tapering body. This projection extends outwardly from the body of the PFJC and is adapted to fit into a connector 106 shaped as a recess on the DPFC 80. The connection between the DPFC 80 and PFJC 90 are similar to the connections discussed in connection with FIGS. 1–6; one difference is the connection in FIGS. 7–9 uses a single connection mechanism or projection and a single connector or recess.

As shown in FIGS. 7–9 then, one advantage of the present invention that the DPFC 80 and the PFJC 90 connect together to form a complete femoral knee prosthesis 110 (see FIG. 9). This prosthesis 110 functions as a traditional one-piece unicompartmental femoral prosthesis. One important advantage of the present invention is that the unicompartmental prosthesis 110 is composed of several modular pieces. Specifically, the prosthesis is composed of two separate, interconnectable pieces, namely a DPFC 80 and a PFJC 90.

Figure 10:
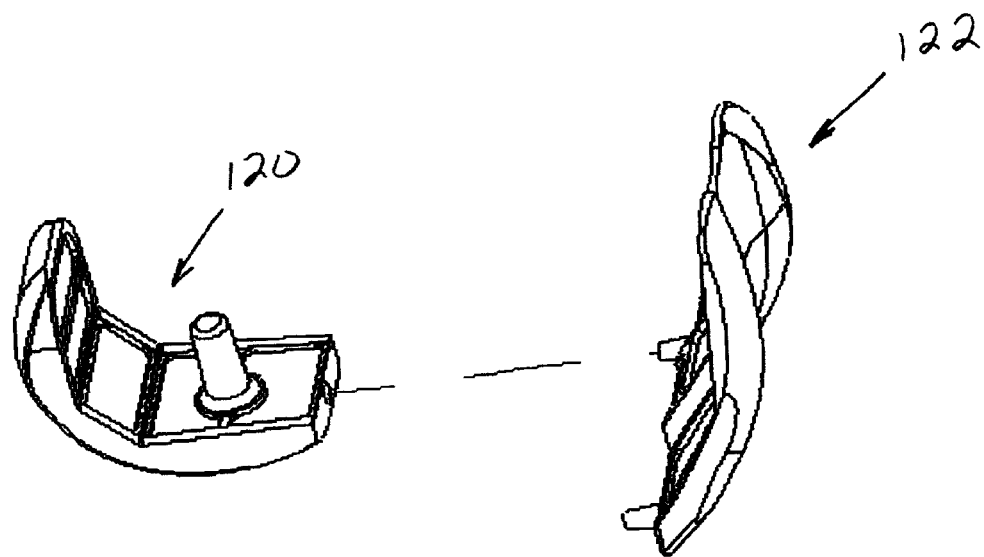
FIG. 10 illustrates an exploded view of a first modular connection of a single medial distal posterior femoral component connecting to a patellar-femoral component with dual condylar surfaces.
Figure 11:
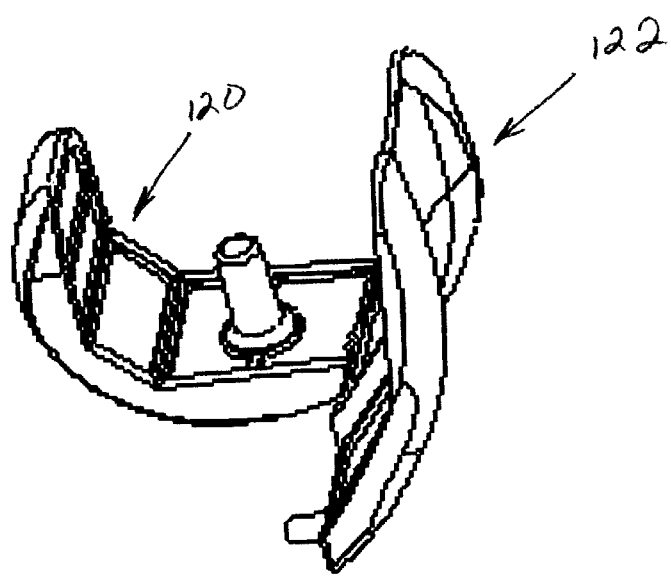
FIG. 11 illustrates a perspective view of the components of FIG. 10 connected together.
Figure 12:
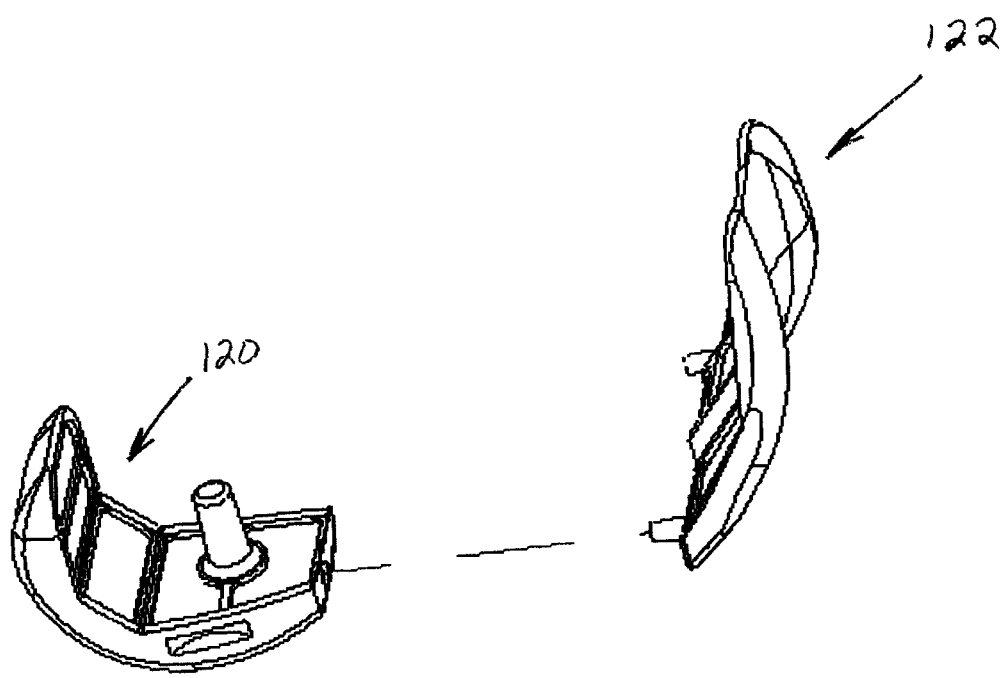
FIG. 12 illustrates an exploded view of a second modular connection of a single medial distal posterior femoral component connecting to a patellar-femoral component with dual condylar surfaces.
Figure 13:
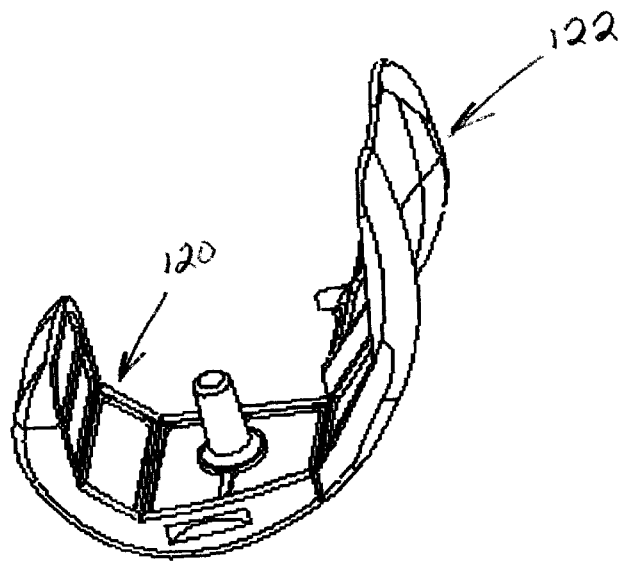
FIG. 13 illustrates a perspective view of the components of FIG. 11 connected together.

FIGS. 10–13 show more examples of the diversification of modularity of the present invention. These figures show a DPFC 120 that is connectable to a PFJC 122. The DPFC 120 is similar to the distal posterior femoral components shown in FIGS. 1 and 2, and PFJC 122 is similar to the patellar-femoral joint component shown in FIGS. 3 and 4. In FIGS. 10 and 11 though, the PFJC 122 connects to a single DPFC 120 on the medial side. By contrast, in FIGS. 12 and 13, the PFJC 122 connects to a single DPFC 120 on the lateral side.

Figure 14:
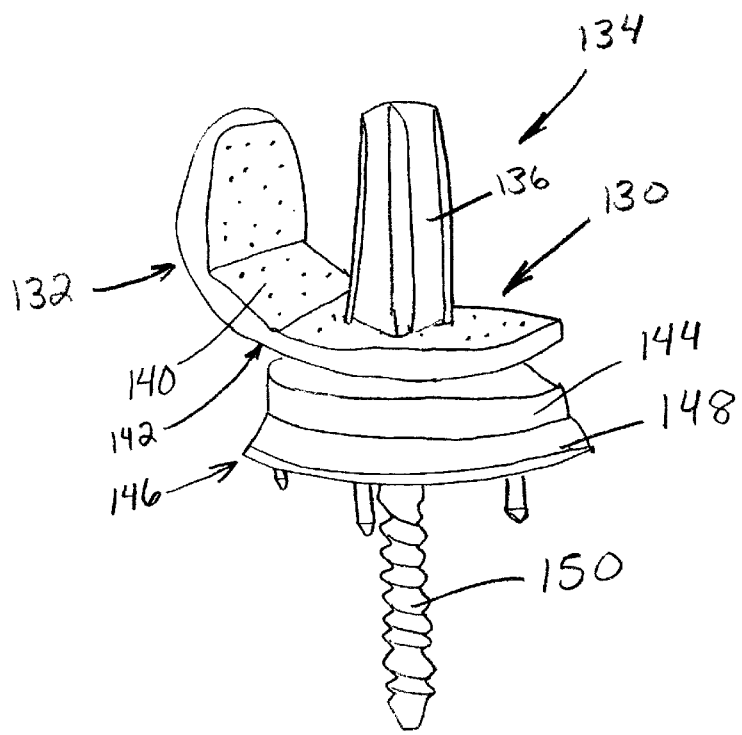
FIG. 14 illustrates a perspective view of a unicompartmental femoral knee with the medial distal posterior femoral component and the patellar-femoral joint component connected to a tibial insert and tibial baseplate.

FIG. 14 shows one example how the modular components of the present invention can be utilized. Here, a DPFC 130 and a PFJC 132 are connected together to form a unicompartmental femoral prosthesis 134. This prosthesis 134 has an extended or enlarged stem 136, but otherwise is generally similar to the unicompartmental prosthesis 110 shown in FIG. 9.

As shown in FIG. 14, the unicompartmental femoral prosthesis 134 has a bone engaging surface 140 with a porous or Cancellous-Structured Titanium (CSTi) coating to enhance bone engagement. An outer articulating condylar surface 142 abuts against a tibial insert 144. This insert 144 is connected to a tibial baseplate 146 having a base portion 148 and threaded screw or stem 150 extending downwardly from the base portion. The tibial insert 144 and baseplate 146 are known to those skilled in the art and may be similar, for example, to those sold by Centerpulse Orthopedics Inc. of Austin, Tex.

Figure 15:
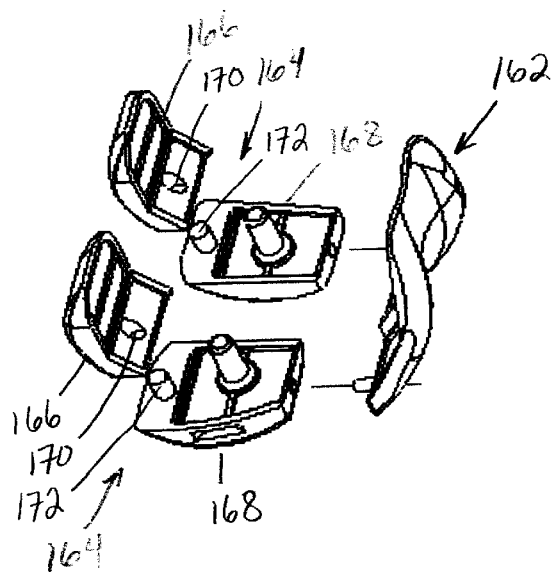
FIG. 15 illustrates a first exploded view of a five-piece femoral knee.
Figure 16:
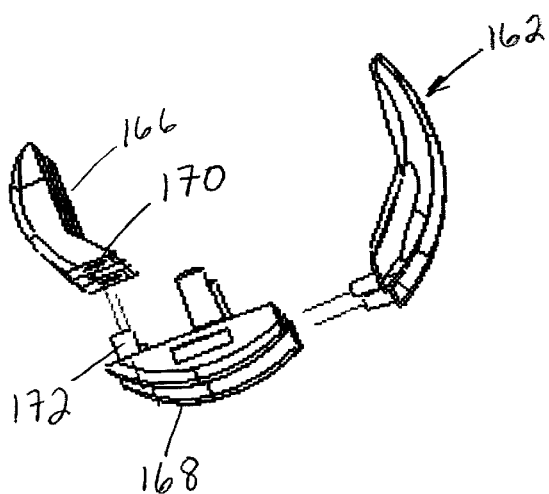
FIG. 16 illustrates a second exploded view of the five-piece femoral knee of FIG. 15.
Figure 17:
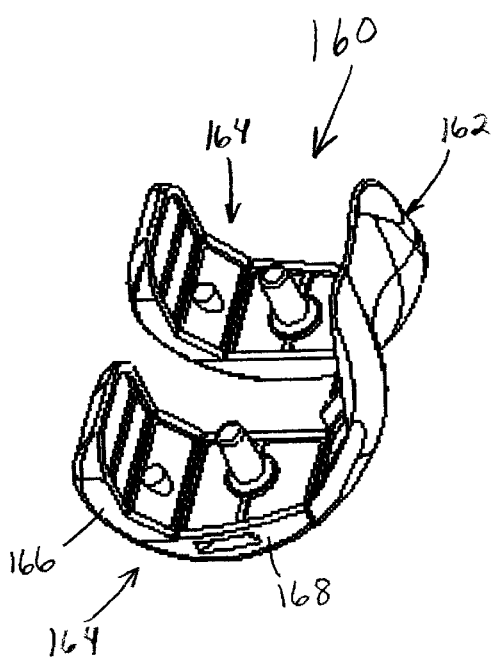
FIG. 17 illustrates a perspective view of the five-piece femoral knee of FIG. 15 wherein the five components are connected together to form a biocompartmental femoral knee.

FIGS. 15–17 show yet more examples of the diversification of modularity of the present invention. Here, a complete femoral knee prosthesis 160 is shown. This prosthesis 160 includes a single PFJC 162 and two DPFC 164 and functions as a traditional bicompartmental prosthesis as shown and described in FIG. 6. As one important difference, each DPFC 164 is formed from two separate components, namely a top half 166 and a bottom half 168. When the top half 166 and bottom half 168 are connected, they function as the DPFC described in FIGS. 1 and 2. Here though, each top half 166 includes a connector 170; and each bottom half includes a connector 172. The connectors 170 and 172 are shown as recesses and projections, respectively, and slideably press-fit together to form single distal posterior femoral components.

As discussed in connection with connection mechanism 54 of PFJC 40 and connectors 28 of DPFC 12 and 14 in FIGS. 5 and 6, the connectors 170 and 172 may have various configurations known to those skilled in the art to achieve a permanent or removable connection between the top half 166 and bottom half 168.

One important advantage of the present invention is that all of the individual, separate distal posterior femoral components and the patellar-femoral joint components are adapted to be used in minimally invasive surgery (MIS) techniques. MIS is intended to allow for the maximum preservation of bone stock, restoration of kinematics, minimal disturbance of the patellar tendon, and rapid rehabilitation postoperatively. During an MIS knee surgery, a three inch incision is made. The DPFC and PFJC are small enough to fit through this incision. Thus, these components can be fit through the incision and then assembled to form a unicompartmental femoral knee, bicompartmental femoral knee, or hybrid of these two (the various embodiments being shown in FIGS. 1–17).

Another advantage of the present invention is the distal posterior femoral components can be made to be completely interchangeable. Thus, no need exists for separate medial/ lateral or left/right components. Further the DPFC and PFJC can be made to have various sizes and thicknesses to accommodate various patient needs. The components can even be coated with CSTi or other coatings known to those skilled in the art to enhance bone growth or cement retention.

As another advantage, the total modular design of the present invention, in addition to being compatible with MIS, allows the surgeon to resurface only the anatomy that requires resurfacing. Thus, the surgeon can assemble a femoral knee prosthesis to better fit the needs of the individual patient and minimize or eliminate unnecessary bone cuts.

Further yet, modularity of the present invention can also save the manufacturer tremendous inventory costs, especially if existing instrumentation can be used. The charts below summarize one potential manufacturing cost savings. The chart on the left shows a typical number of components for a non-modular femoral knee system. The chart on the right shows a typical number of components utilizing the modular components of the present invention. As shown, an inventory can be reduced by approximately 41 components.

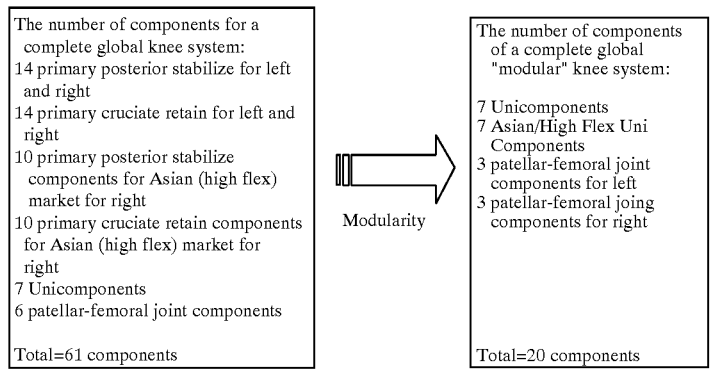

More advantages of the present invention are listed below and are explained in the Summary section:

Full modularity between anterior and distal and posterior femoral components eliminates the need for the surgeon to compromise the patient's natural gait. The system provides the surgeon with flexibility and control in implant sizing.

Multiple distal and posterior components allow multiple ethnic anatomies to be replicated with one knee system. For instance, Asian patients may require longer posterior condyles to replicate their natural anatomy. The option of attaching an Asian unicondylar component to a PFJC will allow the surgeon to convert the prosthesis to allow for high flexion.

A stand-alone patella-femoral component would allow the PFJC to be included in the same system as the primary knee.

A stand-alone distal/posterior component can be used as an MIS unicompartmental prosthesis. Thus the surgeon can make the intraoperative choice of unicompartmental or bicompartmental procedure.

A stand-alone Asian distal/posterior component would allow a unicompartmental or bicompartmental procedure that would closely replicate the Asian anatomy.

Posterior femoral components of two different thickness options may be implanted on the medial and lateral condyles. This option will allow the surgeon to correctly replicate the natural patient anatomy.

An attachment or connection feature and mechanism between the anterior PFJC and the distal components. The attachment allows a surgeon to convert a unicompartmental knee to a primary knee by simply attaching the anterior component to the existing distal/posterior component(s). The attachment features would also allow the surgeon to convert a PFJC to a total knee replacement without revising the PFJC.

While preferred embodiments of this invention have been shown and described, modifications thereof can be made by one skilled in the art without departing from the spirit or teaching of this invention. The embodiments described herein are exemplary only and are not limiting. Many variations and modifications of the system, apparatus, and methods are possible and are within the scope of the inventions claimed below. Accordingly, the scope of protection is not limited to the embodiments described herein, but is only limited by the claims that follow, the scope shall include all equivalents of the subject matter of the claims.

What is claimed is:

1. A tricompartmental femoral knee prosthesis, comprising:
    a medial distal posterior femoral component having a smooth articulating medial surface and a bone engaging medial surface oppositely disposed from the articulating medial surface;
    a lateral distal posterior femoral component having a smooth articulating lateral surface and a bone engaging lateral surface oppositely disposed from the articulating lateral surface; and
    a patellar-femoral component having a smooth articulating patellar-femoral surface and being connected to the medial distal posterior femoral component and the lateral distal posterior femoral component, wherein the patellar-femoral component, the medial distal posterior femoral component, and the lateral distal posterior femoral component are three separate components that connect together to form the tricompartmental femoral knee prosthesis.

2. The tricompartmental femoral knee prosthesis of claim 1 in which the patellar-femoral component is removeably connectable to both the medial distal posterior femoral component and the lateral distal posterior femoral component.

3. The tricompartmental femoral knee prosthesis of claim 2 in which the articulating patellar-femoral surface and the articulating lateral and medical surfaces meet and form a continuous and seamless articulating surface.

4. The tricompartmental femoral knee prosthesis of claim 3 in which the patellar-femoral component includes a connection mechanism adapted to engage and connect to both the medial and lateral distal posterior femoral components.

5. The tricompartmental femoral knee prosthesis of claim 4 in which the medial distal posterior femoral component includes a medial connector adapted to receive the connection mechanism; and the lateral distal posterior femoral component includes a lateral connector adapted to receive the connection mechanism.

6. The tricompartmental femoral knee prosthesis of claim 5 in which the medial and lateral connectors are configured as recesses; and the connection mechanism is configured as two spaced-apart projections, wherein each projection is adapted to fit into one recess.

7. The tricompartmental femoral knee prosthesis of claim 5 in which the medial and lateral connectors are configured as projections and the connection mechanism is configured as two spaced-apart recesses, wherein each projection is adapted to fit into one recess.

8. A femoral knee implant comprising:
    at least three separate components that include two medial distal posterior components and one patellar-femoral component;
    all three components having a smooth outer condylar surface adapted to articulate with a tibial insert and an inner bone-engaging surface adapted to engage bone;
    each medial distal posterior component includes a connector; and
    the patellar-femoral component includes a connection mechanism adapted to engage and connect to each connector.

9. The femoral knee implant of claim 8 in which the connection mechanism and the connectors slideably engage.

10. The femoral knee implant of claim 9 in which the connection mechanism and the connectors press-fit to lock together.

11. The femoral knee implant of claim 8 in which each medial distal posterior component is formed of two separate components that are connectable.

12. The femoral knee implant of claim 4 in which the medial distal posterior component are formed from a top half and a bottom half, wherein the top half and bottom half are removeably connectable together.

* * * * *